United States Patent [19]

Caracciolo

[11] Patent Number: 4,874,435

[45] Date of Patent: Oct. 17, 1989

[54] OZONIZATION OF CONTAINERS

[76] Inventor: Louis D. Caracciolo, 267A Hayesmill Rd., Atco, N.J. 08004

[21] Appl. No.: 138,349

[22] Filed: Dec. 28, 1987

[51] Int. Cl.$^4$ .......................... A61L 2/00; B08B 3/02; B08B 3/08

[52] U.S. Cl. .................... 134/22.18; 134/34; 134/11; 422/24; 422/28; 422/295

[58] Field of Search ................ 134/22.18, 34, 11; 422/24, 28, 295

[56] References Cited

U.S. PATENT DOCUMENTS

| | | | |
|---|---|---|---|
| 594,056 | 12/1896 | Yarnold | 134/22.1 |
| 1,870,318 | 8/1932 | Studdard | 134/34 |
| 2,768,101 | 10/1956 | Fairchild | 134/34 |
| 3,549,528 | 12/1970 | Armstrong | 210/60 |
| 3,985,572 | 10/1976 | Petermann et al. | 134/22.18 |
| 4,018,623 | 4/1977 | Walker | 134/34 |
| 4,314,902 | 2/1982 | Bouk | 208/254 |
| 4,352,740 | 10/1982 | Grader | 210/760 |
| 4,409,188 | 10/1983 | Silberzahn | 422/303 |
| 4,427,455 | 1/1984 | Schepper | 134/22.18 |
| 4,476,010 | 10/1984 | Bouk | 208/15 |
| 4,497,664 | 2/1985 | Verry | 134/34 |
| 4,501,623 | 2/1985 | Till et al. | 134/34 |
| 4,517,159 | 5/1985 | Karlson | 422/20 |

OTHER PUBLICATIONS

Zuern, F., "Weinwirtshaft" (Geiseheim, Fed. R. Ger. 1982.

Rump, H., "Use of Ozone in the Technology of Bottled Water", Ozone: Sci. Eng, 5(2), 95–101 (Eng).

*Primary Examiner*—Patrick P. Garvin
*Assistant Examiner*—George R. Fourson
*Attorney, Agent, or Firm*—Kenyon & Kenyon

[57] ABSTRACT

A process for cleaning the sterilizing containers in which the interior surfaces of a container are subjected to a high power spray of ozonated wiater so as to remove contaminants from the surface and kill yeasts, molds and bacteria which may be beneath the surface. In the case of wooden vessels the process may be carried out so as to remove a veneer of wood from the surface.

8 Claims, No Drawings

OZONIZATION OF CONTAINERS

The invention relates to a method for sterilizing containers constructed of stainless steel, glass or wood by subjecting the surfaces of such containers to a high pressure spray stream of ozonated water. The invention further relates to a method for sterilizing wooden cooperage by spraying the cooperage with ozonated water under high pressure so as to effect a vigorous scrubbing of the wooden surface resulting in a removal of a veneer of wood from the surface.

BACKGROUND OF THE INVENTION

Wooden cooperage is used extensively in the wine making industry and the food industry. Wooden vessels are commonly used to store wine and foods because wood is porous enough to allow the products to slowly breathe thereby promoting slow aging of the products. The use of wooden vessels has the further advantage of allowing tannin, and other organics which occur naturally in wood, to subtly influence the flavor of the stored products.

Unfortunately, the porous nature of wooden cooperage also has the effect of allowing the wood to absorb bacteria, off flavor chemicals and other contaminants. The flavor of wine or food stored in a contaminated or molded vessel can be spoiled. Thus, methods have been developed to clean vessels designed for food storage.

One type of method developed to clean storage containers involves treating a container with an active chemical agent. The chemical agent is removed from the container by treating the container with some type of neutralizing chemical and then rinsing with water. A major disadvantage of these types of methods is that often residual films, comprised of the treating chemicals, remain behind.

Other methods have been developed in which containers have been immersed in baths or ozone and water mixtures or in which containers have been treated with ozone gas. Ozone is an excellent oxidation and sterilization agent which spontaneously decomposes to oxygen. However, the forementioned methods are not completely effective on containers to which hard to remove contaminants have bound. These methods are especially ineffective on wooden vessels because the ozone does not sufficiently penetrate deep beneath the surface of the container where contaminants can be absorbed.

Accordingly, it is an object of the invention to provide a method for sterilizing containers in which the entire inside surface of a container is sprayed with ozonated water under high pressure.

It is another object of the invention to provide a method for sterilizing wooden cooperage in which a veneer of the interior container surface is removed by spraying the surface with a high power stream of ozonated water.

It is a further object of the invention to provide a method for sterilizing containers which does not require the use of a neutralizing agent to neutralize cleaning chemicals.

SUMMARY OF THE INVENTION

Containers are sterilized by spraying their surfaces with a high pressure stream of ozonated water. The process is continued until a course scrubbing of the entire surface of the container is effected.

DETAILED DESCRIPTION

The process of this invention employs ozonated water. The ozone required for the invention may be generated in any of the conventional ways. For example, see U.S. Pat. No. 3,421,999. Preferably, the water is injected with ozone so that the concentration of ozone in water is at least 0.2 parts per million (ppm) however, higher concentrations on the order of 2-5 ppm are most preferred. For this purpose a 2 lb./day USDA approved ozone generator would be sufficient. The ozone may be dissolved in the water to reach this concentration level in accordance with known methods, see for example U.S. Pat. No. 4,352,740.

Ozonated water is rifled at the surfaces of the container to be sterilized. A high impact stream of the ozonated water is shot toward the surfaces to remove soils and contaminants therefrom. In the case of wooden vessels, the ozonated water stream should be sprayed with sufficient speed so that the ozonated water penetrates at least one sixteenth of an inch beneath the surface and preferably at least one eighth of an inch beneath the surface. Generally, spraying the vessel with a water stream under a pressure of 1200-5000 lbs/in$^2$ is sufficient for this purpose. The ozone which is absorbed into the surface naturally decomposes into oxygen and in so doing effects a complete kill of yeasts, molds and bacteria which exist beneath the surface of the wood. The entire surface of the vessel should be treated to ensure complete microbiological sterility.

In the case of wooden vessels, in a preferred embodiment, the ozonated water stream is sprayed at a speed and for a duration which is sufficient to remove a thin veneer of wood from the surface. Generally, spraying the vessel with a water stream under a pressure of 3000 lbs/in$^2$ is sufficient to remove a one eighth of an inch veneer from the surface of a barrel constructed of redwood. Harmful bacteria and other contaminants which have penetrated beneath the surface of the vessel are removed with the veneer of wood by this process. The ozone oxidizes and destroys bacteria which remain. It should be appreciated that thicker veneers of wood may be removed by using higher pressures and by spraying for longer periods. For example, where it is desired to remove one quarter of an inch of redwood from the surface, pressures of up to 5000 lbs/in$^2$ may be necessary. In the case of barrels constructed of softer woods, such as balsa, lower pressures on the order of 300 lbs/in$^2$ may be sufficient.

The spraying apparatus which is required to practice this invention must be of the high pressure type so that the ozonated water stream impacts the surfaces of the containers with force which is sufficient for vigorous scrubbing and/or penetration. For this purpose a chematic C.I.P. (clean in place) system manufactured by Dober Chemical Corp. may be used. This device employs a high-pressure/impingement spray head which removes soils from container surfaces. The spray head is capable of rifling cleaning liquids in concentrated, high-impact stream sprays. A gear-driven turret nozzle rotates in a figure-8 motion so as to clean the entire surface of the container every seven minutes.

Where it is desired to remove a layer of wood from the surface, a model no. 30-60 high pressue spray pump manufactured by Niro Atomizer Co. of Hudson, Wis. may be used.

Once a container is treated according to the process of the invention it should not be used until the ozone has fully decomposed. Where the concentration of ozone in water is between 0.2 to 0.5 ppm ozone decomposition should be complete within 40 minutes. Because ozone naturally decomposes to oxygen, the containers treated according to the process of the invention need not be subjected to a neutralizing agent to neutralize the ozone after treatment. However, after spray treatment, it may be desirable to immerse the containers in a bath of ozonated water in order to rinse off loose contaminants which can remain on the surface of the containers in some cases. The containers may be stored after treatment by filling them with ozonated water.

What is claimed is:

1. A process for cleaning and sterilizing a wooden container comprising the step of spraying the interior surfaces of the wooden container with a stream of ozonated water under a pressure of at least about 1200 lbs/in$^2$ to result in penetration of the ozonated water beneath the surfaces, wherein the concentration of ozone in water is at least 0.2 ppm.

2. The process of claim 1 further comprising the step of rinsing the container with ozonated water.

3. The process of claim 1 in which the step of spraying is conducted so as to remove a veneer of wood from the interior surfaces of the container.

4. The process of claim 1 in which the wooden container is sprayed with the ozonated water under a pressure which is sufficient to cause the ozonated water to penetrate at least one eighth of an inch beneath the surface which is sprayed.

5. A process for cleaning and sterilizing wooden vessels comprising the step of spraying the inner surfaces of the vessels with a stream of ozonated water at a pressure which is sufficient to remove a veneer of wood from the surfaces which is at least one-sixteenth of an inch thick, wherein the concentration of ozone in water is at least 0.2 ppm.

6. The process of claim 5 in which the veneer of wood is at least one quarter of an inch thick.

7. The process of claim 5 wherein the ozonated water is under a pressure of at least about 1200 lbs/in$^2$.

8. The process of claim 6 wherein the ozonated water is under a pressure of at least about 3000 lbs/in$^2$.

* * * * *